(12) United States Patent
Yanagida et al.

(10) Patent No.: US 6,300,481 B1
(45) Date of Patent: Oct. 9, 2001

(54) RARE EARTH COMPLEXES

(75) Inventors: Shozo Yanagida, Kawanishi; Yasuchika Hasegawa, Kyoto; Yuji Wada; Tatsuhiko Yamanaka, both of Toyonaka; Takashi Okubo, Hyogo, all of (JP)

(73) Assignee: New Japan Chemical Co., Ltd. (JP)

( * ) Notice: Subject to any disclaimer, the term of this patent is extended or adjusted under 35 U.S.C. 154(b) by 0 days.

(21) Appl. No.: 09/380,828
(22) PCT Filed: Mar. 10, 1998
(86) PCT No.: PCT/JP98/00970
§ 371 Date: Sep. 10, 1999
§ 102(e) Date: Sep. 10, 1999
(87) PCT Pub. No.: WO98/40388
PCT Pub. Date: Sep. 17, 1998

(30) Foreign Application Priority Data

Mar. 11, 1997 (JP) .................................................... 9-56718

(51) Int. Cl.$^7$ ........................................................ C07F 5/00
(52) U.S. Cl. ................................................. 536/16; 534/15
(58) Field of Search ................................ 534/15, 16, 7, 534/10–14

(56) References Cited

U.S. PATENT DOCUMENTS 5,554,664   9/1996   Lamanna et al. .................. 522/25

OTHER PUBLICATIONS

Allen R. Siedle, Richard A. Newmark, Louis H. Pignolet and Richard D. Howells, Protonation of Organometallic Hydrdes with Fluorochemical Acids, Journal of Americna Chemical Society (1984), vol. 106, pp. 1510–1511.

*Primary Examiner*—Dameron L. Jones
(74) *Attorney, Agent, or Firm*—Larson & Taylor, PLC

(57) ABSTRACT

The present invention provides an optically functional material comprising a rare-earth complex represented by the formula (I)

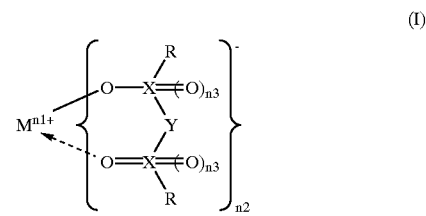

wherein M is a rare-earth atom, $n_1$ is 2 or 3, $n_2$ is 2, 3 or 4, R is a $C_1$–$C_{20}$ group containing no H, X is a Group IVA atom, Group VA atom other than nitrogen or Group VIA atom other than oxygen, $n_3$ is 0 or 1, and Y is C-Z' (wherein Z' is D, a halogen or $C_1$–$C_{20}$ group containing no H), N, P, As, Sb or Bi, or by the formula (II)

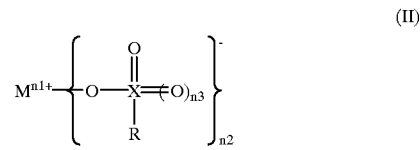

wherein N, R, X, $n_1$, $n_2$ and $n_3$ are as defined above.

6 Claims, 2 Drawing Sheets

(a) POS (b) Nd(POS)₃

RARE EARTH COMPLEXES

This is a 371 of Application No. PCT/JP98/00970, filed Mar. 10, 1998.

TECHNICAL FIELD

The present invention relates to rare-earth complexes, ligands useful for these complexes, optically functional materials comprising the rare-earth complex, and a process for preparing the rare-earth complex.

BACKGROUND ART

With remarkable advances in developing electronic materials, many developments have been made in optically functional materials in the field of optoelectronics. For example, neodymium-containing glass has been introduced into actual use in laser beam electronic devices, whereas the glass has found only limited use because of the difficulties encountered in producing and working the glass and a high production cost. The dye laser, which can be used in the form of a solution, has the excellent features of being inexpensive, easy to work and cool and continuously usable for a prolonged period of time. However, the dye laser is low in strength and therefore limited in application.

On the other hand, organic optical materials such as polyphenylene have the drawback of being short in luminescence life and diminished in the effectiveness of luminescence although superior to inorganic optical materials in workability.

It is already known that a complex [$Nd^{III}(HFA)_3$] comprising $Nd^{3+}$ and three molecules of hexafluoroacetylacetone (HFA) coordinated therewith and having heavy hydrogen substituted for the hydrogen of active methylene luminesces in the state of a solution [S. Yanagida et al., J. Phys. Chem., 100, 10201(1996)]. This complex is short in luminescence life and low in quantum yield and decomposes in the presence of a very small amount of water to lose its optical conversion function. It has therefore been desired to develop complexes having a high luminescence intensity and good stability.

An object of the present invention is to provide rare-earth complexes having excellent luminescence characteristics, compounds useful as ligands for these complexes, optically functional materials containing the rare-earth complex and a process for preparing such rare-earth complexes.

DISCLOSURE OF THE INVENTION

Figure 1:
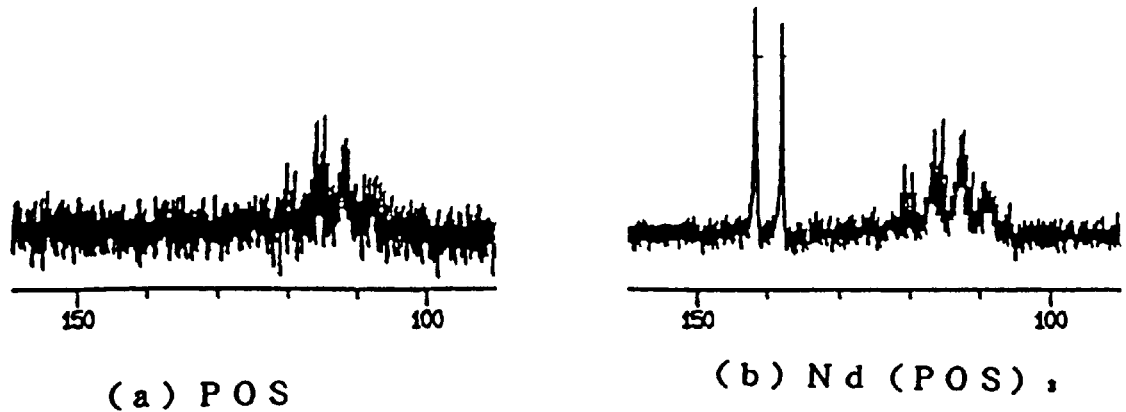
FIG. 1 shows $^{13}$C-NMR spectra of (a) POS and (b) Nd(POS)$_3$.

The present invention relates to rare-earth complexes given below, compounds useful as ligands for these complexes, optically functional materials containing the rare-earth complex, and a process for preparing the rare-earth complex.

Item 1. An optically functional material comprising a rare-earth complex represented by the formula (I)

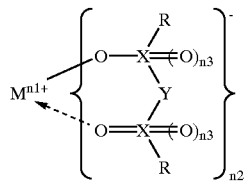

wherein M is a rare-earth atom, $n_1$ is 2 or 3, $n_2$ is 2, 3 or 4, R's are the same or different and are each a $C_1$–$C_{20}$ group containing no hydrogen atoms, X is a Group IVA atom other than carbon atom, Group VA atom other than nitrogen or Group VIA atom other than oxygen, $n_3$ is 0 or 1, and Y is C-Z' (wherein Z' is heavy hydrogen, a halogen atom or $C_1$–$C_{20}$ group containing no hydrogen atoms), N, P, As, Sb or Bi, or by the formula (II)

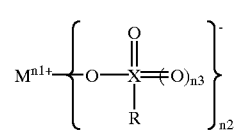

wherein M, R, X, $n_1$, $n_2$ and $n_3$ are as defined above.

Item 2. A rare-earth complex represented by the formula

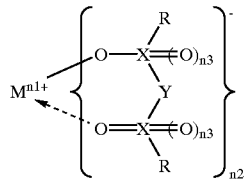

wherein M, R, X, $n_1$, $n_2$ and $n_3$ are as defined above.

Item 3. A rare-earth complex represented by the formula (IIa)

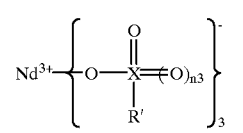

wherein R', X and $n_3$ are as defined above.

Item 4. A method of causing luminescence of rare-earth complexes comprising the step of irradiating a solvent solution, dispersion or suspension of a rare-earth complex according to Item 2 or 3 with light.

Item 5. A compound represented by the formula (III)

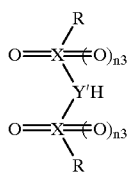
(III)

wherein X, Y', R and $n_3$ are as defined above except where the two R's are each $CF_3$, and where one of the R's is $CF_3$ and the other R is $C_4F_9$.

Item 6. A process for preparing a rare-earth complex represented by the formula (I):

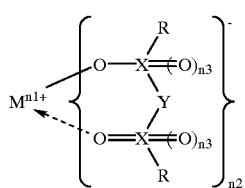
(I)

wherein M, R, X, $n_1$, $n_2$ and $n_3$ are as defined above, the process comprising mixing together a compound represented by the formula (III)

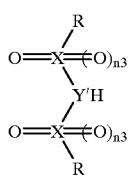
(III)

wherein X, Y', R and $n_3$ are as defined above and at least one rare-earth metal compound selected from the group consisting of a rare-earth metal oxide, rare-earth metal alkoxide, rare-earth metal amide and rare-earth metal salt (and further mixing the resulting complex in $D_2O$, $CD_3OD$ or like solvent permitting heavy hydrogen substitution when Y' is CH).

The present invention is embodied preferably as follows.

Item A. An optically functional material according to Item 1, a rare-earth complex according to Item 2 or 3, or a compound according to Item 5 wherein R is perhalogenated alkyl or perhalogenated alkenyl having one or a plurality of —O—, —COO—, —OCO— and —CO— interposed between a C—C single bond thereof in an optional position to give an ether, ester or ketone structure.

Item B. An optically functional material according to Item 1, a rare-earth complex according to Item 2 or 3, or a compound according to Item 5 wherein R is perfluorinated alkyl or perfluorinated alkenyl.

Item C. An optically functional material according to Item 1, a rare-earth complex according to Item 2 or 3, or a compound according to Item 5 wherein X is S, P or Se, and $n_3$ is 1.

Item D. An optically functional material according to Item 1, or a rare-earth complex according to Item 2 or 3 wherein M is Nd, Yb, Tb or Eu.

Item E. An optically functional material according to Item 1, or a rare-earth complex according to Item 2 or 3 wherein Y is C—D, C—Cl, C—F, C—Br, C—I, N or P.

Item F. An optically functional material according to Item 1, a rare-earth complex according to Item 2 or 3, or a compound according to Item 5 wherein R is perhalogenated alkyl or perhalogenated alkenyl.

Item G. A compound according to Item 5 wherein Y' is CH, N or P.

According to the invention, examples of $C_1$–$C_{20}$ groups represented by R and containing no hydrogen atoms are:

straight-chain or branched perhalogenated alkyl groups such as perfluoroalkyl ($C_nF_{2n+1}$; n=1–20) and perchloroalkyl ($C_nCl_{2n+1}$; n=1–20), straight-chain or branched $C_2$–$C_{20}$ perhalogenated alkenyl groups such as perfluoroalkenyl (perfluorovinyl, perfluoroallyl, perfluorobutenyl, etc.) and perchloroalkenyl, straight-chain or branched $C_2$–$C_{20}$ perhalogenated alkynyl groups such as perfluoroalkynyl and perchloroalkynyl, $C_3$–$C_{20}$ perhalogenated cycloalkyl groups such as perfluorocycloalkyl ($C_nF_{2n-1}$; n=3–20) and perchlorocycloalkyl ($C_nCl_{2n-1}$; n=3–20), $C_3$–$C_{20}$ perhalogenated cycloalkenyl groups such as perfluorocycloalkenyl (perfluorocyclopentenyl, perfluorocyclohexenyl, etc.) and perchlorocycloalkenyl, $C_6$–$C_{20}$ perhalogenated aromatic groups such as perfluorophenyl, perchlorophenyl, perfluoronaphthyl, perchloronaphthyl and perhalogenated biphenyl, $C_6$–$C_{20}$ perhalogenated heteroaromatic groups such as perfluoropyridyl and perfluoropiperazinyl, and perhalogenated aralkyl groups such as perfluorobenzyl and perfluorophenethyl.

When required, the rare-earth complex of the formula (I) or (II) wherein R is perfluoroalkenyl may be polymerized with a perfluoroolefin having 1 to 20 carbon atoms, such as tetrafluoroethylene or hexafluoropropylene, to obtain a high-molecular-weight rare-earth complex.

One or more halogen atoms attached to the aromatic ring of the above-mentioned perhalogenated aromatic group, perhalogenated heteroaromtic group or perhalogenated aralkyl group may be replaced by a substituent containing no hydrogen atoms, such as cyano, nitro, nitroso, $C_1$–$C_4$ perhalogenated alkoxyl, $C_2$–$C_5$ perhalogenated alkoxycarbonyl or $C_2$–$C_{20}$ perhalogenated alkylcarbonyloxy.

The $C_1$–$C_{20}$ perhalogenated alkyl, $C_2$–$C_{20}$ perhalogenated alkenyl or $C_2$–$C_{20}$ perhalogenated alkynyl may have one or a plurality of —O—, —COO— and —CO— interposed between a C—C single bond thereof in an optional position to give an ether, ester or ketone structure.

Examples of rare-earth elements represented by M are the elements of the lanthanum series, i.e., La, Ce, Pr, Nd, Pm, Sm, Eu, Gd, Tb, Dy, Ho, Er, Tm, Yb and Lu, among which preferable are Nd, Eu, Tb and Yb.

X is one of Group IVA atoms such as Si, Ge, Sn and Pb, Group VA atoms other than N and including P, As, Sb and Bi, and Group VIA atoms other than O and including S, Se, Te and Po, and is preferably S, P or Se. Y is N, P, As, Sb or Bi, and is preferably N or P.

$n_1$ is 2 or 3, preferably 3.

$n_2$ is. 2 to 4, preferably 2 or 3, more preferably 3.

$n_3$ is 0 or 1, preferably 1. $n_3$ is 1 especially when X is S.

The ligand of the formula (III) to be incorporated into the complex of the invention is prepared, for example, in the following manner.

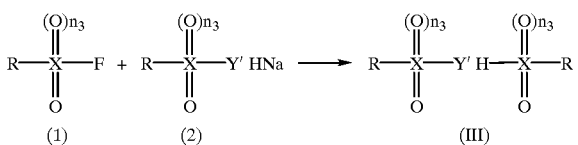

wherein R, X, Y and $n_3$ are as defined above.

A compound (2) is reacted with hexamethyldisilazane for trimethylsilylation, and the resulting compound is reacted with a compound (1) to obtain the desired compound of the formula (III). The reaction Eproceeds favorably when effected for about 1 to about 5 hours at room temperature to a temperature generally permitting reflux of the solvent, using about 1 to about 1.1 moles of hexamethyldisilazane and about 1 mole of the compound (1) are used per mole of the compound (2).

The complex of the present invention represented by the formula (I) can be prepared by mixing together the compound represented by the formula (III) and at least one rare-earth metal compound selected from the group consisting of a rare-earth metal oxide, rare-earth metal hydroxide, rare-earth metal alkoxide, rare-earth metal amide and rare-earth metal salt, for example, in a solvent.

More specifically, the rare-earth complex represented by the formula (I) can be prepared by the process to be described below.

The ligand of the formula (III) is dissolved in a solvent, the rare-earth metal compound (particulate, granular or in any other form) is added to the solution, and the mixture is stirred at room temperature to 100° C. for about 1 hour to about 100 hours. The product is then purified as by crystallization or liquid-liquid extraction, whereby the rare-earth complex can be obtained. The complex may further be recrystallized from a solvent such as chloroform or methanol.

Examples of rare-earth metal oxides useful as rare-earth metal compounds are trivalent compounds $M_2O_3$ (wherein M is a rare-earth atom), while other oxides such as MO and $M_4O_7$ are also usable. Similarly, examples of rare-earth metal hydroxides include $M(OH)_{n_1}$; examples of rare-earth metal alkoxides include $M(OR^1)_{n_1}$ (wherein $R^1$ is alkyl); examples of rare-earth metal amides include $M(NR^aR^b)_3$ (wherein $R^a$ and $R^b$ are the same or different and are each hydrogen, alkyl or phenyl); and examples of rare-earth metal salts include $M^{3+}(Z)_{n_1}$ {wherein Z is an anion such as chlorine ion, bromine ion, iodine ion, fluorine ion, ½ sulfate ion, nitrate ion, acetate ion or like monocarboxylate ion, ½ (oxalate ion, succinate ion, malonate ion or like dicarboxylate ion), ⅓ (citrate or like tricarboxylate ion) or ⅓ phosphate ion}. $n_1$ is as defined above.

The solvent to be used in preparing the complex of the formula (I) is not limited specifically but can be any solvent such as a protic solvent or aprotic solvent. Examples of useful protic solvents are water and alcoholic solvents such as methanol and ethanol. Examples of useful aprotic solvents are acetone, methyl ethyl ketone and like ketone solvents, diethyl ether, tetrahydrofuran and like ether solvents, chloroform, methylene chloride and like halogen solvents, DMSO, DMF, etc. Preferable among these is water. The solvent is used in an amount, for example, of about 1 to about 100 parts by weight, preferably about 1 to about 20 parts by weight, relative to the combined amount of the ligand and the rare-earth metal compound (taken as 1 part by weight).

The complex of the formula (II) can be obtained by reacting the rare-earth metal compound with an equivalent or excess of $R—X(=O)_{n_3+1}$ (OH), which is a known substance, in water. The complex of the formula (II) is susceptible to coordination with $H_2O$, loses the properties for use as an optically functional material when having coordinated $H_2O$ and is therefore less stable to $H_2O$ than the complex of the formula (I). If incorporating coordinated $H_2O$, the complex of the formula (II) can be treated with $D_2O$ when to be used to remove the $H_2O$ for use as an optically functional material.

The rare-earth metal compound is used for preparing the rare-earth complex of the formula (I) in an amount of 1 to 10 equivalents, preferably 1.05 to 3 equivalents, per equivalent of the ligand of the formula (III). The rare-earth complex of the formula (II) can be prepared from the compounds mentioned as used in a similar mixing ratio.

In the case where the rare-earth complex represented by the formula (II) contains coordinated water, the complex is treated, for example, in the following manner. MeOD is added to a sample of the complex, the sample/MeOD mixture is frozen and then allowed to stand in a vacuum at room temperature for about 24 hours, and the methanol is subsequently distilled off to convert the coordinated $H_2O$ to $D_2O$. The complex sample substituted with heavy hydrogen is thereafter dissolved in a dry organic solvent containing no hydrogen atoms (with all hydrogen atoms replaced by heavy hydrogen, halogen atoms or the like) for use as an optically functional material. Organic solvents containing heavy hydrogen, such as DMSO, methanol, acetone, THF, DMF and chloroform which are substituted with heavy hydrogen, or hydrogen-free solvents such as carbon tetrachloride are desirable since these solvents give complex a prolonged luminescence life.

The rare-earth complex represented by the formula (I) is especially preferable since the complex is usable as dissolved directly in a dry solvent containing no hydrogen atoms without necessitating any procedure for converting coordinated $H_2O$ to $D_2O$. On the other hand, the rare-earth complex represented by the formula (II) requires the conversion of the coordinated $H_2O$ to $D_2O$.

Examples of solvents for use in the luminescence method of the invention for dissolving the complex of the formula (I) are ketone compounds such as acetone and methyl ethyl ketone, lower alcohols such as methanol and ethanol, water, ethers such as ether, THF, isopropyl ether, aromatic hydrocarbons such as benzene and toluene, hydrocarbon halides such as chloroform, carbon tetrachloride and tetrachloroethane, DMF, DMSO, acetamide, formamide and esters such as ethyl acetate, glycols such as ethylene glycol and propylene glycol, etc.

The solvent may be one containing hydrogen atoms such as DMSO or acetone, whereas organic solvents containing heavy hydrogen, such as DMSO, methanol, acetone, THF, DMF and chloroform which are substituted with heavy hydrogen, or hydrogen-free solvents such as carbon tetrachloride are desirable since these solvents give complex a prolonged luminescence life.

In place of the organic dye of an organic dye laser, the rare-earth complex of the present invention is usable as an optically functional material (element, electronic device or the like) under the same conditions as the organic dye laser. For example, the rare-earth complex of the invention is usable as dissolved, dispersed or suspended in a solvent under the specified conditions as to concentration (about 0.00001 to about 1 mole/liter, preferably about 0.005 to about 0.5 mole/liter, more preferably about 0.01 to about 0.3 mole/liter) and temperature (−50° C. to room temperature).

Although usable in the form of a liquid, the complex of the invention can also be used as an optically functional material in a solid state, for example, as dissolved or dispersed in a polymer.

The complex of the present invention achieves a high optical conversion efficiency and is useful as a novel laser material for use in optical devices such as CD players, optical disks, facsimile systems, remote controllers, copying machines, laser printers, large-sized displays, medical lasers, laser beam machining and measuring means and devices relating to printing. Stated more specifically, the complex is applicable to laser devices, light-emitting diodes, liquid crystals, optical fibers, optical sensors, solar cells, etc.

The complex of the invention can be adapted to alter the wavelength of the laser beam when modified or changed in the structure of ligand and/or in the kind of rare-earth element, affording a laser for giving a beam of desired wavelength. Unlike semiconductors, the complex of the invention can be used for preparing laser materials by a greatly simplified process without necessitating a clean room or the like.

THE BEST MODE FOR CARRYING OUT THE INVENTION

The present invention will be described below in detail with reference to Examples, to which the invention is not limited.

EXAMPLE 1

Preparation of $C_6F_{13}SO_2NHSO_2C_6F_{13}$ (PHS)

To 18 mmoles of $C_6F_{13}SO_2NHNa$ was added dropwise $[(CH_3)_3Si]_2NH$ (18 ml, 86.5 mmoles) in a nitrogen atmosphere. With addition of 2 ml of dioxane, the mixture was refluxed at 120° C. for 8 hours, and the $[(CH_3)_3Si]_2NH$ was distilled off, followed by drying in a vacuum for 12 hours. A 30 ml quantity of dry acetonitrile and $C_6F_{13}SO_2F$ (21 mmoles) were added to the mixture, and the resulting mixture was refluxed at 100° C. for 48 hours. The acetonitrile was thereafter distilled off, and sulfuric acid was used for protonation, followed by extraction with ether and sublimation, giving the desired product (a white solid, 30% in yield).

IR (cm$^{-1}$): 1369 (S=Ost.), 1237 (C-Fst.), 1208 (C-Fst.), 1152 (S=Ost.); $^{19}$F-NMR (acetone-d$_6$, standard substance $C_6F_6$; ppm): −79.51 (3F), −111.65 (2F), −118.56 (2F), −120.27 (2F), −121.21 (2F), −124.67 (2F); MS (m/Z): 780 ($[C_6F_{13}SO_2]_2N^-$, very strong); Elemental analysis ($C_{12}H_2O_4N_2F_{26}$).

|  | C | H | N |
| --- | --- | --- | --- |
| Calculated | 18.45 | 0.13 | 1.79 |
| Found | 18.45 | 0.08 | 2.05 |

EXAMPLE 2

Preparation of $C_8F_{17}SO_2NHSO_2C_8F_{17}$ (POS)

$C_8F_{17}SO_2NHSO_2C_8F_{17}$ (white solid, 12% in yield) was prepared in the same manner as in Example 1 with the exception of using $C_8F_{17}SO_2NHNa$ and $C_8F_{17}SO_2F$ in place of $C_6F_{13}SO_2NHNa$ and $C_6F_{13}SO_2F$, respectively.

IR (cm$^{-1}$): 1373 (S=Ost.), 1237 (C-Fst.), 1206 (C-Fst.), 1151 (S=Ost.); $^{19}$F-NMR (acetone-d$_6$, standard substance $C_6F_6$; ppm): −79.51 (3F), −111.59 (2F), −118.43 (2F), −120.10 (6F), −121.06 (2F), −124.59 (2F).

EXAMPLE 3

Preparation of $C_4F_9SO_2NHSO_2C_4F_9$ (PBS)

$C_4F_9SO_2NHSO_2C_4F_9$ (white solid, 26% in yield) was prepared in the same manner as in Example 1 with the exception of using $C_4F_9SO_2NHNa$ and $C_4F_9SO_2F$ in place of $C_6F_{13}SO_2NHNa$ and $C_6F_{13}SO_2F$, respectively.

IR (cm$^{-1}$): 1373 (S=Ost.), 1237 (C-Fst.), 1206 (C-Fst.), 1151 (S=Ost.); $^{19}$F-NMR (acetone-d$_6$, standard substance $C_6F_6$; ppm): −79.31 (6F), −111.47 (4F), −119.18 (4F), −124.19 (4F).

EXAMPLE 4

Preparation of $C_8F_{17}SO_2NHSO_2C_4F_9$ (POBS)

To 18 mmoles of $C_9F_{17}SO_2NHNa$ was added dropwise $[(CH_3)_3Si]_2NH$ (18 ml, 86.5 mmoles) in a nitrogen atmosphere. With addition of 2 ml of dioxane, the mixture was refluxed at 120° C. for 8 hours, and the $[(CH_3)_3Si]_2NH$ was distilled off, followed by drying in a vacuum for 12 hours. A 30 ml quantity of dry acetonitrile and $C_4F_9SO_2F$ (21 mmoles) were added to the mixture, and the resulting mixture was refluxed at 100° C. for 48 hours. The acetonitrile was thereafter distilled off, and sulfuric acid was used for protonation, followed by extraction with ether and sublimation, giving the desired product (a white solid, 10% in yield).

IR (cm$^{-1}$): 1369 (S=Ost.), 1237 (C-Fst.), 1208 (C-Fst.), 1152 (S=Ost.).

EXAMPLE 5

Preparation of Nd(POS)$_3$ complex

The $C_8F_{17}SO_2NHSO_2C_8F_{17}$ (0.8 g, 0.82 mmole) obtained in Example 2 was dissolved in 30 ml of distilled water, Nd$_2$O$_3$ (46 mg, 0.14 mmole) was added to the solution, and the mixture was stirred at room temperature for 3 days. The resulting solid precipitate was filtered off, washed with water and dissolved in methanol, followed by centrifuging and filtration to remove the unreacted Nd$_2$O$_3$. The methanol was removed from the product by distillation, affording the desired complex (Nd(POS)$_3$; white solid). The complex obtained was found to be free from water by differential thermal analysis (DSC).

IR (cm$^{-1}$): 3449 (O-Hst.), 1368 (S=Ost.), 1237 (C-Fst.), 1150 (S=Ost.); $^{19}$F-NMR (acetone-d$_6$, standard substance $C_6F_6$; ppm) −79.33 (3F), −111.24 (2F), −118.07 (2F), −119.81 (6F), −120.78 (2F), −124.29 (2F).

FIG. 1 shows $^{13}$C-NMR spectra.

The two signals around 140 ppm in FIG. 1, (b) Nd(POS)$_3$ indicate CF$_2$ adjacent to S subjected to resonance.

Figure 2:
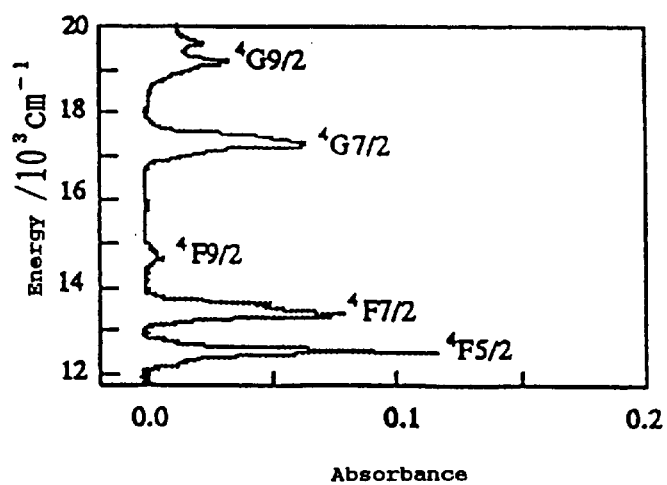
FIG. 2 shows an absorption spectrum of Nd(POS)$_3$ in CD$_3$OD.

FIG. 2 shows the absorption spectrum of Nd(POS)$_3$ in heavy methanol.

Incidentally, Nd(PHS)$_3$ complex is obtained in the same manner as above with the exception of using $C_6F_{13}SO_2NHSO_2C_6F_{13}$ obtained in Example 1 in place of $C_8F_{17}SO_2NHSO_2C_8F_{17}$ prepared in Example 2.

Further the use of $C_4F_9SO_2NHSO_2C_4F_9$ obtained in Example 3 or $C_8F_{17}SO_2NHSO_2C_4F_9$ obtained in Example 4 affords Nd(PBS)$_3$ complex or Nd(POBS)$_3$ complex.

EXAMPLE 6

Preparation of Eu(POS)$_3$ Complex

The $C_8F_{17}SO_2NHSO_2C_8F_{17}$ (0.8 g, 0.82 mmole) obtained in Example 2 was dissolved in 30 ml of distilled water, Eu$_2$O$_3$ (50 mg, 0.14 mmole) was added to the solution, and the mixture was stirred at room temperature for 3 days. The resulting solid precipitate was filtered off, washed with water and dissolved in methanol, followed by centrifuging and filtration to remove the unreacted Eu$_2$O$_3$. The methanol was removed from the product by distillation, affording the desired complex (Eu(POS)$_3$; white solid). The complex obtained was found to be free from water by differential thermal analysis (DSC).

IR (cm$^{-1}$): 1354 (S=Ost.), 1237 (C-Fst.), 1209 (S-Fst.), 1056 (S=Ost.); $^{19}$F-NMR (acetone-d$_6$, standard substance C$_6$F$_6$; ppm): −79.2 (3F), −111.33 (2F), −118.15 (2F), −119.87 (4F), −120.8 (2F), −124.29 (2F).

EXAMPLE 7
Preparation of Tb(POS)$_3$ Complex

The desired complex (Tb(POS)$_3$; white crystals) was prepared in the same manner as in Example 6 with the exception of using Tb$_4$P$_7$ (60 mg, 0.82 mmole) as the rare-earth metal compound. The complex obtained was found to be free from water by differential thermal analysis (DSC).

IR (cm$^{-1}$): 1353 (S=Ost.), 1243 (C-Fst.), 1208 (C-Fst.), 1056 (S=Ost.); $^{19}$F-NMR (acetone-d$_6$, standard substance C$_6$F$_6$; ppm) −79.3 (3F), −111.1 (2F), −118.0 (2F), −119.9 (4F), −120.9 (2F), −124.4 (2F).

EXAMPLE 8
Preparation of Nd(O$_3$SCF$_3$)$_3$

Nd$_2$O$_3$ (1 mole) was added to an aqueous solution of CF$_3$SO$_3$H (2 moles), and the mixture was allowed to stand at room temperature, causing crystals to separate out. The crystals, which were reddish purple and needlelike, were filtered off and dried in a vacuum for 2 days, giving the desired Nd(O$_3$SCF$_3$)$_3$. TG-DTA revealed that the crystals obtained were a hexahydrate.

Elemental analysis (NdC$_3$H$_{12}$O$_{15}$F$_9$S$_3$)

|  | C | H |
|---|---|---|
| Calculated | 5.15 | 1.73 |
| Found | 5.01 | 1.82 |

IR (cm$^{-1}$): 3449 (O-Hst.), 1638 (O-H5), 1263 (C-Fst.), 1180 (S-Ost.); $^{19}$F-NMR (acetone-d$_6$, standard substance C$_6$F$_6$; ppm): −77.03

EXAMPLE 9
Preparation of Nd(O$_3$SC$_8$F$_{17}$)$_3$·6D$_2$O

A 30 ml quantity of 0.34M aqueous solution of pentafluorooctanesulfonic acid was added to 0.56 g (1.72 mmoles) of Nd$_2$O$_3$, and the mixture was stirred at room temperature for 24 hours to obtain a purple solid. The solid product was filtered off, washed with water and recrystallized from a chloroform-methanol solvent mixture, giving purple needle-like crystals, which were then dried at 5 mm Hg for 2 days. Yield 30%. TG-DTA revealed that the crystals obtained were a hexahydrate.

IR (cm$^{-1}$): 3432 (O-Hst.), 1637 (O-Hδ), 1241 (C-Fst.), 1204 (C-Fst.), 1152 (S-Ost.); $^{19}$F-NMR (acetone-d$_6$, standard substance C$_6$F$_6$; ppm): −79.61 (3F), −112.85 (2F), −119.16 (2F), −120.30 (6F), −121.19 (2F), −124.67 (2F).

The Nd(O$_3$SC$_8$F$_{17}$)$_3$·6H$_2$O (80 mg) obtained was dissolved in CD$_3$OD (2.0 ml), and the solution was deaerated at −78° C. and further allowed to stand at room temperature for 24 hours. Subsequently, the CD$_3$OD was distilled off, giving Nd(O$_3$SC$_8$F$_{17}$)$_3$·6D$_2$O. The compound was found to contain D$_2$O substituting for H$_2$O by H-NMR.

Figure 3:
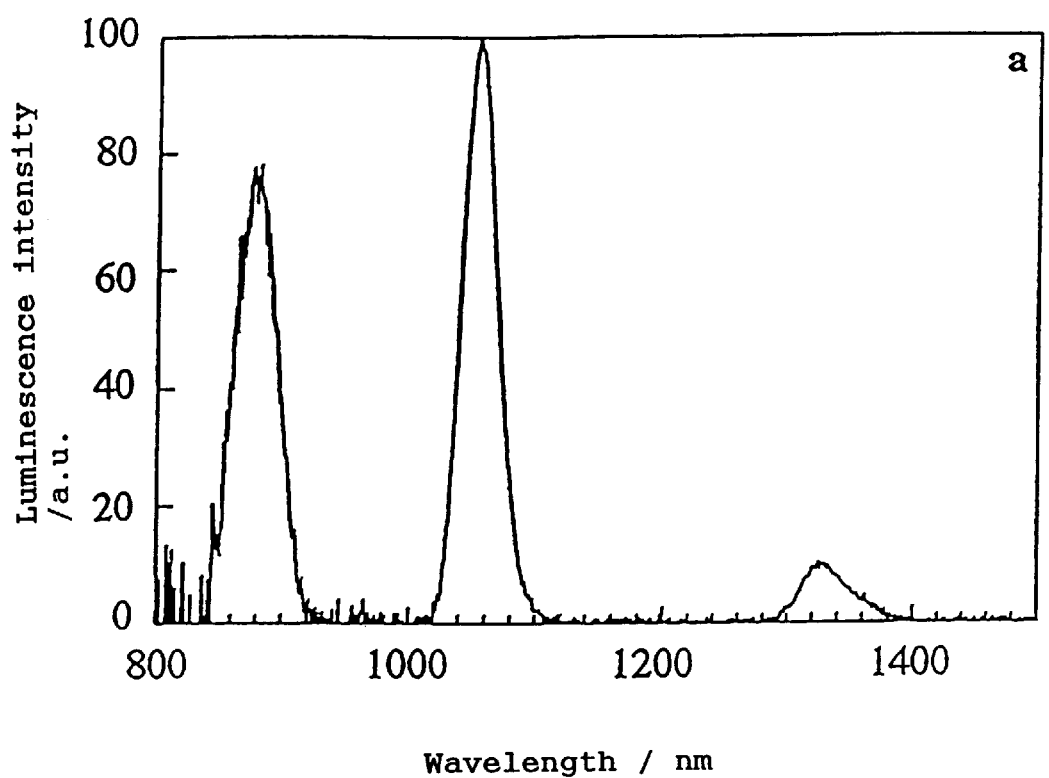
FIG. 3 is a luminescence spectrum of Nd(POS)$_3$ in acetone-d$_6$.

EXPERIMENTAL EXAMPLE
Nd(POS)$_3$, Eu(POS)$_3$, Tb(POS)$_3$, Nd(PHS)$_3$, Nd(PBS)$_3$, Nd(POBS)$_3$ and Nd(O$_3$SC$_8$F$_{17}$)$_3$ were checked for luminescence characteristics in acetone-d$_6$ or DMSO-d$_6$. Table 1 shows the results. FIG. 3 shows the luminescence spectrum of Nd(POS)$_3$ in acetone-d$_6$.

Incidentally, Nd(CF$_3$CO-CD-COCF$_3$)$_3$ (hereinafter referred to as Nd(HFA)$_3$) was prepared according to Chemical Physics Letters, 248, pp. 8–12, 1996. The complexes were used at a concentration of 0.05 mole/liter.

TABLE 1

| Complex/solvent | Excitation wavelength (nm) | Luminescence wavelength (μm) | Quantum yield (%) | Luminescence life (μs) |
|---|---|---|---|---|
| Nd(POS)$_3$/acetone-d$_6$ | 585 | 1.06 | 3.2 | 13 |
| Eu(POS)$_3$/DMSOd$_6$ | 394 | 0.618 | 56.8 | 1500 |
| Tb(POS)$_3$/acetone-d$_6$ | 325 | 0.545 | — | — |
| Nd(PHS)$_3$/acetone-d$_6$ | 585 | 1.06 | 3.2 | 13 |
| Nd(PBS)$_3$/acetone-d$_6$ | 585 | 1.06 | 2.5 | 1 |
| Nd(POBS)$_3$/acetone-d$_6$ | 585 | 1.06 | 3.0 | — |
| Nd(HFA)$_3$/acetone-d$_6$ | 585 | 1.06 | 0.3 | 1.7 |
| Nd(O$_3$SC$_8$F$_{17}$)$_3$/DMSO-d$_6$ | 585 | 1.06 | 3.4 | 15.3 |

The mark "—" indicates that no measurement was made.

EXPERIMENTAL EXAMPLE 2

Nd(POS)$_3$ was checked for luminescence characteristics in acetone. The complex concentration was 0.05 mole/liter. The result is as follows: excitation wavelength =585 nm, luminescence wavelength =1.06 μm, quantum yield =3.0%, and luminescence life =4 μs. The complex exhibited the same luminescence spectrum as shown in FIG. 3.

Table 1 reveals that the Nd complexes of the invention [Nd(POS)$_3$ and Nd(O$_3$SC$_8$F$_{17}$)$_3$] are higher in quantum yield and more excellent in luminescence characteristics for use as optically functional materials than the conventional complex [Nd(HFA)$_3$]. Experimental Example 2 further shows that the complex of the invention luminesces also in a solvent having hydrogen atoms. Like the Nd complexes, Eu, Tb and other rare-earth complexes also have outstanding luminescence characteristics.

What is claimed is:

1. An optically functional material comprising a rare-earth complex represented by formula (I)

$$M^{n1+} \left\{ \begin{array}{c} O-X(=O)_{n3} \\ | \\ Y \\ | \\ O=X(=O)_{n3} \end{array} \right\}_{n2} \quad (I)$$

wherein M is a rare-earth atom, n$_1$ is 2 or 3, n$_2$ is 2, 3 or 4, R's are the same or different and are each a C$_1$–C$_{20}$ group containing no hydrogen atoms, X is a Group IVA atom other than carbon atom, Group VA atom other than nitrogen or Group VIA atom other than oxygen, n$_3$ is 0 or 1, and Y is C-Z' wherein Z' is heavy hydrogen, a halogen atom or C$_1$–C$_{20}$ group containing no hydrogen atoms, N, P, As, Sb or Bi, or by the formula (II)

(II)

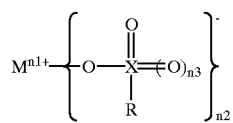

wherein M, R, X, $n_1$, $n_2$, and $n_3$ are as defined above.

2. A rare-earth complex represented by formula (I)

(I)

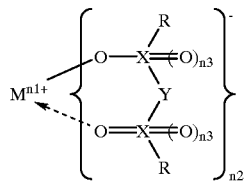

wherein M, R, X, Y, $n_1$, $n_2$ and $n_3$ are as defined in claim 1.

3. A rare-earth complex represented by formula (IIa)

(IIa)

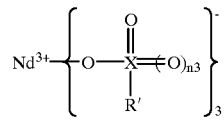

wherein R' is a $C_2$–$C_{20}$ group containing no hydrogen atoms, X and $n_3$ are as defined in claim 1.

4. A method of luminescence of the rare-earth complex of claim 2 comprising irradiating a solution, dispersion or suspension of the rare-earth complex with light.

5. A process for preparing a rare-earth complex represented by formula (I)

wherein M, R, X, Y, $n_1$, $n_2$ and $n_3$ are as defined above, the process comprising mixing together a compound represented by formula (III)

(III)

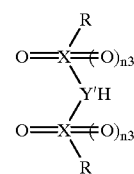

wherein Y' is C-$Z_1$' wherein $Z_1$' is hydrogen, heavy hydrogen, a halogen atom or $C_1$–$C_{20}$ group containing no hydrogen atoms, N, P, As, Sb or Bi and wherein X, R and $n_3$ are as defined in claim 1 and at least one rare-earth metal compound selected from the group consisting of a rare-earth metal oxide, rare-earth metal alkoxide, rare-earth metal amide and rare-earth metal salt, and further mixing the resulting complex in $D_2O$, $CD_3OD$ or like solvent permitting heavy hydrogen substitution when Y' is CH.

6. A method of luminescence of the rare-earth complex of claim 3 comprising irradiating a solution, dispersion or suspension of the rare-earth complex with light.

\* \* \* \* \*